(12) United States Patent
Lundkvist et al.

(10) Patent No.: US 9,060,753 B2
(45) Date of Patent: Jun. 23, 2015

(54) SAMPLING SYSTEM

(71) Applicant: APROVIX AB, Uppsala (SE)

(72) Inventors: Ulf Lundkvist, Uppsala (SE); Berndt Sjoberg, Sodertajle (SE); Erik Wilander, Uppsala (SE); Soren Nygren, Knivsta (SE)

(73) Assignee: APROVIX AB (SE)

( * ) Notice: Subject to any disclaimer, the term of this patent is extended or adjusted under 35 U.S.C. 154(b) by 0 days.

(21) Appl. No.: 14/072,969

(22) Filed: Nov. 6, 2013

(65) Prior Publication Data

US 2014/0066807 A1 Mar. 6, 2014

Related U.S. Application Data

(63) Continuation of application No. 11/920,462, filed as application No. PCT/IB2006/001723 on May 26, 2006, now abandoned.

(60) Provisional application No. 61/685,892, filed on May 31, 2005.

(51) Int. Cl.
*A61B 10/02* (2006.01)
*A61B 10/00* (2006.01)
*A61B 17/00* (2006.01)

(52) U.S. Cl.
CPC ......... *A61B 10/0096* (2013.01); *A61B 10/0051* (2013.01); *A61B 10/0291* (2013.01); *A61B 2010/0003* (2013.01); *A61B 2010/0074* (2013.01); *A61B 2017/00473* (2013.01)

(58) Field of Classification Search
CPC .................. A61B 2010/02; A61B 2010/0216; A61B 2010/0225; A61B 10/02; A61B 10/0291; A61B 2017/320004–2017/320012

USPC .................................. 600/569–572; 604/1–3
See application file for complete search history.

(56) References Cited

U.S. PATENT DOCUMENTS

| | | | |
|---|---|---|---|
| 2,608,894 A | 9/1952 | Miller et al. | |
| 3,485,236 A * | 12/1969 | Frost | 600/570 |
| 3,838,681 A | 10/1974 | Dalton | |
| 3,995,618 A | 12/1976 | Kingsley et al. | |
| 4,027,658 A * | 6/1977 | Marshall | 600/570 |
| 4,165,755 A * | 8/1979 | Cassai | 132/218 |
| 5,137,090 A | 8/1992 | Hare et al. | |
| 5,445,164 A | 8/1995 | Worthen et al. | |
| 5,477,863 A | 12/1995 | Grant | |
| 5,787,891 A * | 8/1998 | Sak | 600/569 |
| 6,007,498 A * | 12/1999 | Buck et al. | 600/572 |
| 6,042,552 A | 3/2000 | Cornier | |
| 6,352,513 B1 * | 3/2002 | Anderson et al. | 600/572 |
| 6,435,017 B1 | 8/2002 | Nowicki, Jr. et al. | |
| 2003/0028123 A1 * | 2/2003 | Pevoto | 600/562 |

FOREIGN PATENT DOCUMENTS

| | | |
|---|---|---|
| EP | 0235673 | 9/1987 |
| WO | 02070644 | 9/2002 |
| WO | 03026502 | 4/2003 |

* cited by examiner

*Primary Examiner* — Max Hindenburg
*Assistant Examiner* — John Pani
(74) *Attorney, Agent, or Firm* — Gearhart Law LLC

(57) ABSTRACT

A sampling system comprises a mailing package; a cell sampling device comprising a flexible shaft having a handle at one end, wherein the shaft is configured to allow an individual to self collect a cell sample from mucous tissue, and a sample collecting element removably connectable with the other end of the shaft and operable to collect a cell sample from mucous tissue of an individual; and a sealable unit, wherein the unit is configured to store the sample collecting element having a cell sample thereon configured to receive the remaining components of the system for delivery to a user.

17 Claims, 6 Drawing Sheets

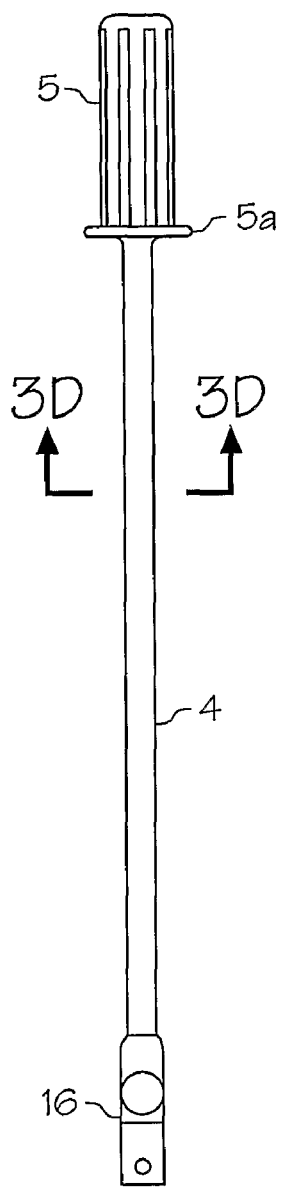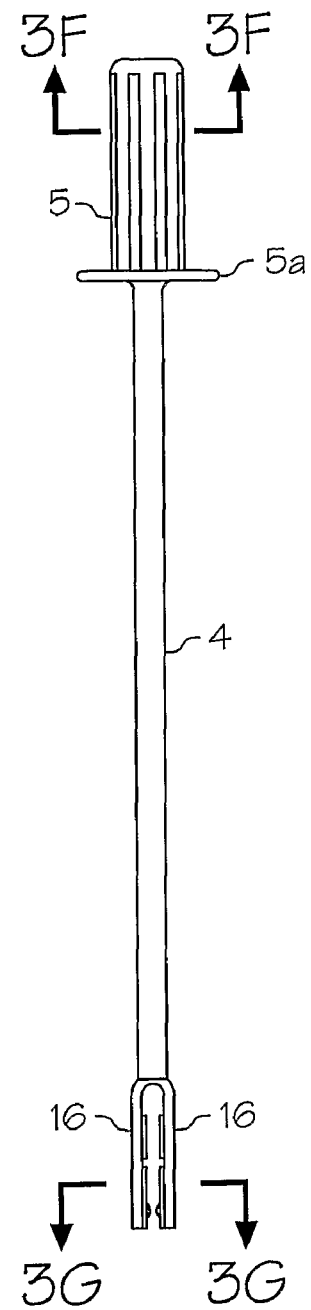
FIG. 3C
FIG. 3E

SAMPLING SYSTEM

PRIORITY CLAIM

This application is continuing application Ser. No. 11/920,462, which was filed on Nov. 15, 2007 and which was a national application of PCT/IB2006/0017 filed on May 26, 2006 and which claimed priority of U.S. 60/685,892 filed on May 31, 2005. The contents of each of which are incorporated herein by reference in their entirety.

FIELD OF THE INVENTION

The present invention relates generally to the field of screening and health control. More specifically the invention relates to a novel sampling system and associated methods suitable, for example, in testing to detect virus-associated cervical cancer, microbial infections and pathological changes.

BACKGROUND OF THE INVENTION

Cervical cancer is the second most common form of cancer in women world-wide. Invasive cervical carcinoma develops by progression of less severe epithelial changes, known as dysplacia and cervical intraepithelial neoplacia (CIN I-II-III), into cervical carcinomas in situ (CIS).

Using vaginal aspirates (Pap smears), the epithelial changes can be detected and classified by common cytological methods. It is particularly important to notice that invasive cervical carcinoma is preceded by its dysplastic precursor lesions, which can be present for months or years before cervical carcinoma develops. Furthermore, progression to carcinoma can effectively be stopped by a simple operation (conization) if the precursor lesions are detected.

Many developed countries have experienced up to a 50% reduction in the incidence of and mortality from invasive cervical carcinoma after the introduction of organized screening programs. Despite this fact, about 500,000 women in the world are struck by cervical cancer each year. In the U.S., close to 5,000 women die each year from this disease. This number would drop further if more women were tested on a regular basis.

Of those who die of cervical cancer, 50% have not had a Pap test done in 5 or more years. Indeed, those women who do not participate in the gynecological health control and those who show false negative cytology are the highest risk groups for cervical cancer. The efficacy and reliability of the sampling method and the sample's analysis are therefore primary issues. This involves, in the first place, reaching those women who do not now participate in the gynecological screening by providing a simple and reliable device for sampling, and secondly, to increase the discriminating efficacy of the analytical methods to diagnose infections, precancerous lesions or cancerous lesions.

Association between papillomavirus (HPV) infection and cervical carcinoma was postulated in the 1970's. The International Biological Study on Cervical Cancer reported a world-wide prevalence of infection with HPV of 93% in women with invasive cervical cancer. In addition, the subtypes HPV 16 and HPV 18 are the most significant risk factors in its aetiology. HPV infection is also an important risk factor for progression of CIN.

Recent studies with improved methods of polymerase chain reaction (PCR) imply an overall HPV prevalence of almost 100% and that the PCR results correlate with the histological findings. These results reinforce the rational for HPV testing in combination with, or even instead of, cytology in population-based screening programs.

Determination of squamous intraepithelial lesions, or cervical dysplacia, is commonly used as an indication of progression to cervical cancer. Alternatively, the presence of HPV nucleic acid in a patient sample, following amplification by PCR, is taken as a risk factor for progression to cervical cancer. From the above, it is obvious that cytology and PCR analysis of HPV infection provide very efficient means to detect individuals at risk to develop cervical cancer.

Recently published evidence-based consensus guidelines for the management of women with cervical cytological abnormalities and cervical cancer precursors state that women with atypical squamous cells of undetermined significance (ASCUS) should be managed using a program of 2 repeat cytology tests, immediate colposcopy, or DNA testing for high-risk types of HPV. Testing for HPV DNA is the preferred approach when liquid-based cytology is used for screening.

The limiting factor in order to further decrease the incidence of and mortality from cervical cancer appears therefore to be related to reaching the non attending women and providing a simple sampling device giving relevant samples for HPV analysis and/or cytology.

Traditionally, sampling of vaginal smear requires scraping of a woman's cervix with a sampling device, such as a spatula or a brush. This sampling is generally performed by medical professionals like gynecologists, midwifes or nurses in a clinical environment. Many women, who now refrain from such gynecological testing, would participate if the sampling could be carried out at home and/or by the women themselves. Self and home sampling would therefore increase the participation in the gynecological screening, and by that means, decrease the incidence of cervical cancer.

In addition to the above, sampling systems are also in demand for DNA analysis. Law enforcement officials, paternity agents, etc. are constantly taking DNA samples to help solve crimes, determine paternity, etc. As the results of the tests done on these samples dramatically affect people's lives and may be desired as evidence in legal proceedings, the sampling must be done in a manner in which the sample contamination is reduced or avoided. As such, there is a need for an improved sampling system.

SUMMARY OF THE INVENTION

In view of the need for an improved sampling device and a system easily adaptable to present health screening procedures, the present invention therefore provides improvement over the currently available devices and systems.

In one embodiment, the present invention comprises a sampling system comprising: a) a mailing package; b) a cell sampling device comprising: i) a flexible shaft having a handle at one end, wherein the shaft is configured to allow an individual to self collect a cell sample from mucous tissue, and ii) a sample collecting element removably connectable with the other end of the shaft and operable to collect a cell sample from mucous tissue of an individual; and c) a sealable unit, wherein the unit is configured to store the sample collecting element having a cell sample thereon and to be received within the mailing package in its sealed form. The sampling system may optionally further include a transport package configured to receive components a)-c) for delivery to a user.

In another embodiment, the present invention comprises a sampling system comprising: a) a mailing package; b) an instruction sheet; c) a flexible shaft; d) a sample collecting element connected with an end of the shaft and having a plurality of raised portions and grooves; e) a bar coded unit including an air tight cover and configured to receive the sample collecting element therein and to be received in the mailing package; and f) a bar-coded transport package configured to receive components a)-e) for delivery to a user.

The sampling systems of the invention may be used by medical personnel for patient sampling and/or may be used by individuals for self-sampling. The sampling systems are particularly advantageous for use by an individual in conduct self-sampling in testing to detect, for example, virus-associated cervical cancer, microbial infections and pathological changes. These and additional embodiments and advantages may be more fully apparent in view of the detailed description.

BRIEF DESCRIPTION OF THE DRAWINGS

The present invention will be more fully understood from the detailed description, given herein below and the accompanying drawings which are given for illustration, and thus not limiting the scope of the invention, and wherein:

FIGS. 3A-3J show schematic plan and cross-sectional views of a sampling device included in one embodiment of a sampling system according to the invention.

Figure 1A:
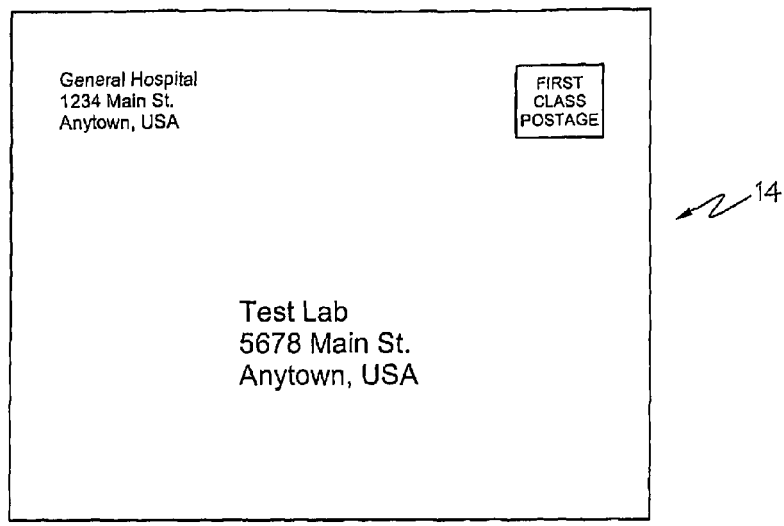
FIGS. 1A and 1B are, respectively, a front view of mailing package and a rear view of a bar-coded transport package included in one embodiment of the sampling system according to the invention.
Figure 1B:
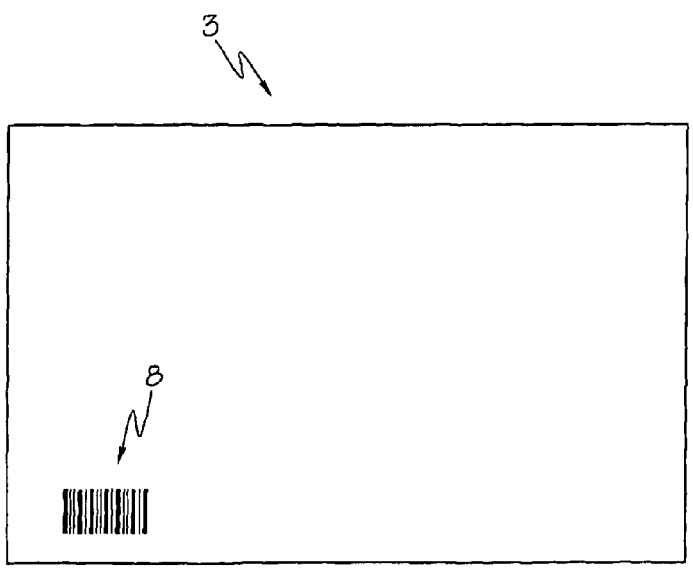

The embodiments set forth in the drawings are illustrative in nature and are not intended to be limiting of the invention defined by the claims. Moreover, individual features of the drawings and the invention will be more fully apparent and understood in view of the following detailed description.

DETAILED DESCRIPTION

The present invention provides a sampling system that overcomes disadvantages of prior art devices, instruments and procedures for obtaining cell samples from mucous tissue such as, but not limited to, the gynecological tract and the mouth.

In a first aspect, the present invention provides a sampling system which may be employed by an individual to easily and reliably, at home or at a visit to a medical location, under hygienic conditions, take cell smears and samples, for example, gynecological samples, from mucous tissues. The samples can be transported without risk of contamination or transmission of infective agents, and thereafter be analyzed by chemical methods, such as PCR, or by other microbiological methods.

With reference to FIGS. 1-4, the sampling system according to one embodiment of the present invention includes a cell sampling device 2 for taking cell samples, a mailing package 14 for returning a sample to, for example, a laboratory for testing, and a sealable unit 7. Optionally, the sampling system may include a transport package 3 for delivery of the sampling system components to a user. One embodiment of the transport package 3 is shown in FIG. 1B, and includes a bar code, for use as described in further detail below. One embodiment of the mailing package 14, including a printed address for mailing a sample to the appropriate medical professional, on the front side thereof is shown in FIG. 1A. It will be appreciated that the transport package 3 and the mailing package 14 may be provided with this exemplary information, or other information as desired, in any suitable arrangement. The mailing package 14 allows return of the sealable unit 7 and contents thereof to the appropriate facility, for example, by mail, courier or the like, without compromising the sealable unit or its contents.

In one embodiment, the cell sampling device 2 comprises a shaft 4 having a handle 5 at one end. The handle may include a lower lip 5a as shown to facilitate the ease of use of the device. The shaft 4 is configured to allow an individual to self collect a cell sample from mucous tissue. In a specific embodiment, the shaft 4 is configured to allow an individual to self collect a sample from a cervix location. In an additional embodiment, at least a portion of the shaft is flexible, and in a further embodiment, a portion of the shaft 4 is rigid. Alternatively, the shaft may be entirely flexible. Reference to a flexible shaft is intended to mean at least a portion of the shaft is flexible, hi another embodiment, the shaft 4 is formed of a polymer, including, for example, polypropylene, polyethylene, or a mixture thereof.

Figures 3A, 3B:
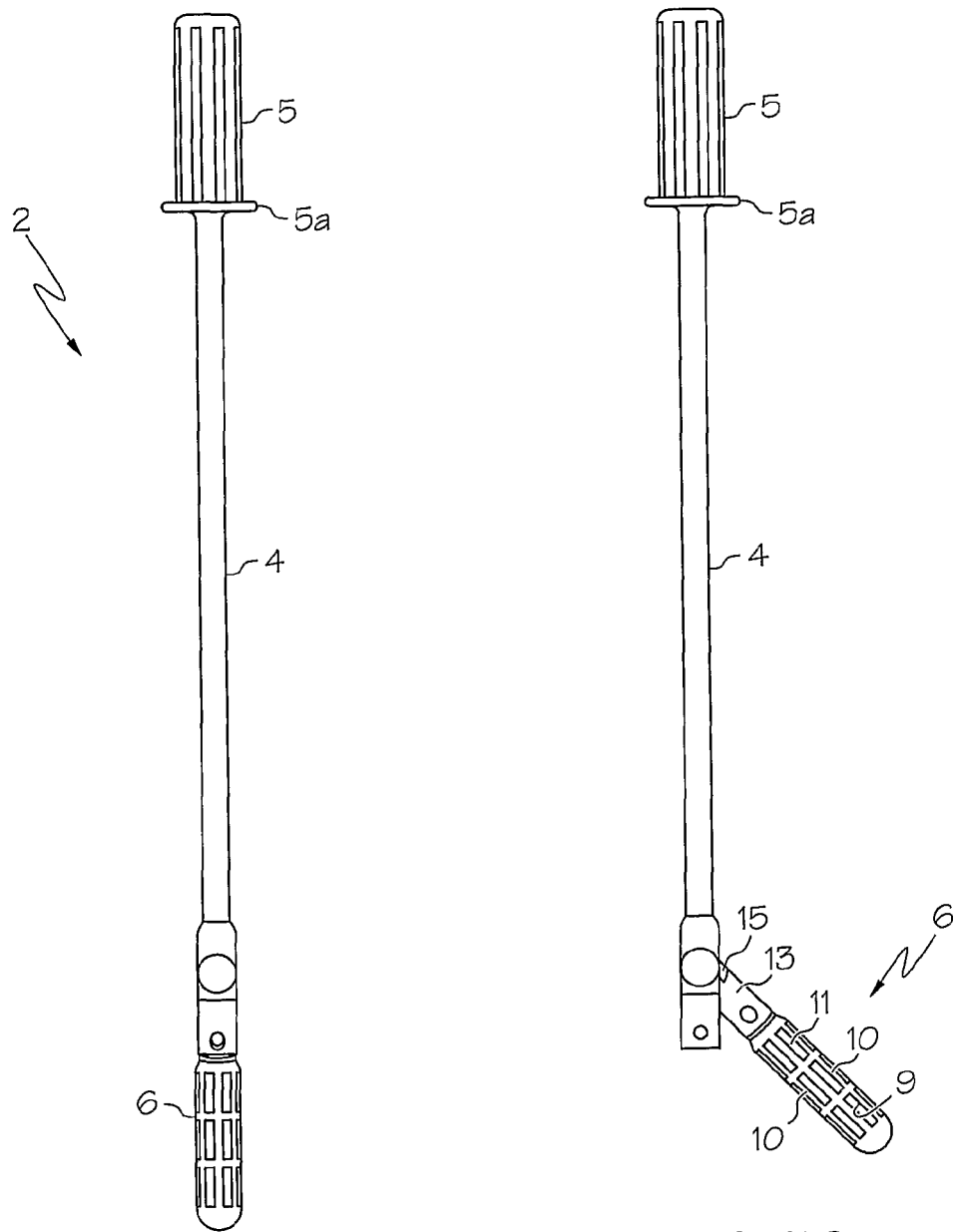
Figure 3D:
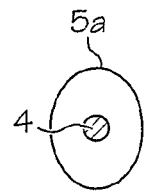
Figure 3F:
Figure 3G:
Figure 3H:
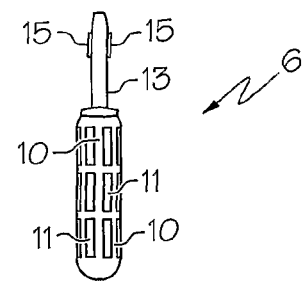
Figure 3I:
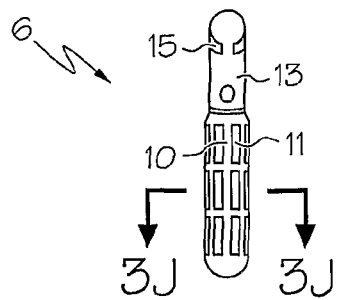
Figure 3J:
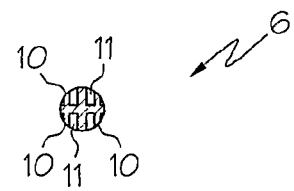

The cell sampling device 2 further comprises a sample collecting element 6 removably connectable with the other end of the shaft 4 opposite the handle. The element 6 is operable to collect a cell sample from mucous tissue of an individual. FIGS. 3A and 3B show the sample collecting element 6 removable connected with the shaft 4, while FIGS. 3C and 3E show the shaft 4 without the sample collecting element 6 thereon and FIGS. 3H and 3I show the sample colleting element 6 apart from the shaft 4. FIG. 3D shows a cross-sectional view taken along line D-D in FIG. 3C; FIGS. 3F and 3G show cross-sectional views taken along lines F-F and G-G in FIG. 3E, respectively, and FIG. 3J shows a cross-sectional view taking along line J-J in FIG. 3I.

The sealable unit 7 is configured to store the sample collection element 6 having a cell sample thereon, preferably in a manner which prevents contamination of the element 6, i.e., in an air tight manner, and to be received within the mailing package 14 in its sealed form. In one specific embodiment, the unit 7 is a sealable tube.

In an additional embodiment, the transport package 3 and the unit 7 each have an identification element 8, for example correlating to the individual from which a sample is made. In a further embodiment, the identification element 8 consists of a bar code.

The shaft 4, the adsorbing sample collecting element 6, the sealable unit 7, and the unit cover 12 can be manufactured of any suitable materials as desired. For example, these components may be formed of the same or different plastic materials. In a further embodiment, a plastic material of the cell sampling device 2, preferentially polypropylene, is selected with a flexural modulus giving the shaft 4 flexibility to follow the anatomy of the vagina to reach portio vaginalis and at the same time rigid enough to get a close contact between the sample collecting element 6 and the mucous tissue ectocervix.

In a specific embodiment as shown in FIGS. 3A, 3B and 3H-3J, the sample collecting element 6 is generally cylindrical. The element 6 may be configured and sized as desired for a particular sample collection. In one embodiment, the element 6 is generally cylindrical as shown and has a diameter from about 2 to about 20 mm. In one embodiment as shown in FIGS. 3A, 3B, 3H and 3I, the front part of the sample collecting element 6 is rounded and may be made very smooth, so as to render it more tissue friendly and easier for introduction into the sensitive tissue of the vagina.

In a further embodiment, the sample collecting element 6 comprises at least one raised portion 9. In another embodiment, the raised portions of the sample collecting element 6 form a plurality of cell and mucous adsorbing segments 10. The segments 10 are separated by at least one groove 11 or a plurality of grooves 11. In a specific embodiment, the grooves 11 are from about 0.01 to 2 mm in width and in another embodiment, the raised portions 9 include an edge at the groove 11 capable of scraping tissue to collect a sample. In an additional embodiment, the raised portions 9 forming the segments 10 and the grooves 11 are configured to collect a cell sample and hold the sample within the grooves 11 even during withdrawal of the device 2 from a body orifice. In a specific embodiment, the segments 10 of the sample collecting element 6 have an unpolished surface and, in a specific embodiment, comprise an abrasive surface, for example having a surface roughness of about 1 to 100 μm, to facilitate release of cell-containing mucous, for example, from ectocervix tissue.

In one embodiment, the raised portions 9 form segments 10 which are essentially rectangular in shape by providing the grooves 11 in the longitudinal and transversal directions on the sample collecting element 6. However, it is of course possible to provide grooves 11 in other geometries, e.g. in spiral or zigzag patterns. In one embodiment, the grooves 11 are substantially narrower than the width of the raised portions 9. hi one embodiment the width of the grooves 11 does not exceed about 2 mm, and in another embodiment, the width is from about 0.5 to about 0.1 mm. Importantly, the grooves 11 should be able to absorb mucous liquid and cells therein, and maintain these materials in place during retraction of the device from the body orifice.

Figure 2:
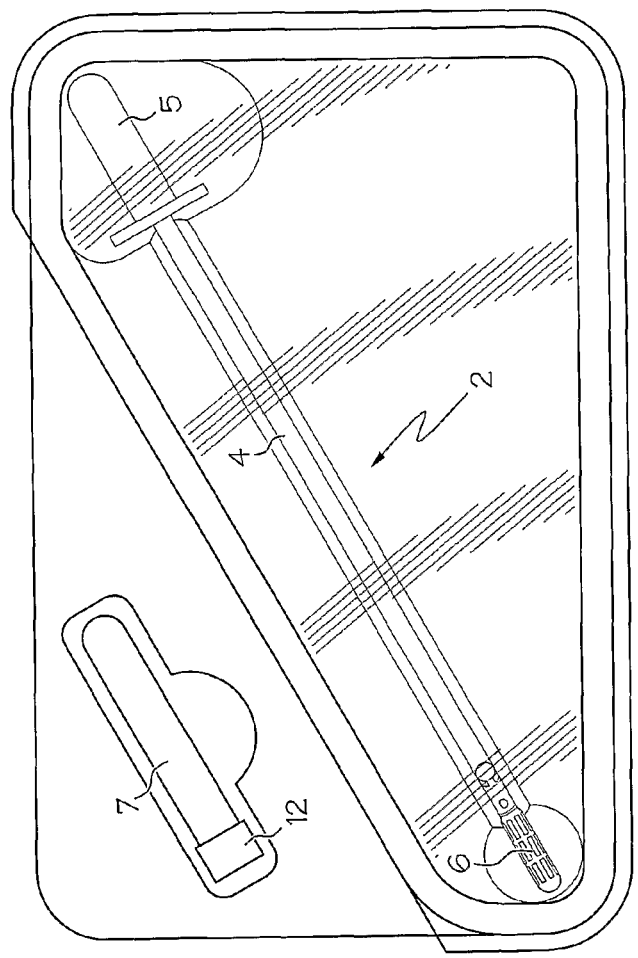
FIG. 2 is a top view of a sampling device and a sealable unit held in a protective plastic tray, in accordance with one embodiment of the sampling system of the invention.

The sample collecting element 6 is removably connected with one end of the shaft 4. Thus, the sample collecting element 6 may be connected with the shaft to facilitate obtaining a mucous sample, for example from ectocervix tissue, and may then be removed from the shaft 4 for insertion in the sealable unit 7. One of ordinary skill in the art will appreciate that various connection configurations may be employed to facilitate the removable connection of the sample collecting element 6 with the end of the shaft 4. In the specific embodiments shown in FIG. 3A-3J, an end of the sample collecting element 6 is provided with an extension 13 having protrusions 15. The end of the shaft 4 is correspondingly provided with extensions 16 having grooves adapted to receive protrusions 15 therein in a snap-fit manner. Thus, the extension 13 is inserted between the extensions 16 in a male-female type manner in which the protrusions 15 are snap fit within grooves contained in the extension 16 at the end of the shaft 4. The protrusions are released from the grooves contained in extension 16 by rotation of the sample collecting element 6 as shown in FIG. 3B. As a result, the sample collecting element 6 may be removed from the shaft 4 to the unit 7 and preferably sealed therein, for example with a unit cover 12 as shown in FIG. 2. Advantageously, to prevent contamination of the sample collecting element 6 once a mucous sample is adhered thereto, the sample collecting element may be at least partially inserted within the unit 7, prior to removal of the sample collecting element 6 from the shaft 4. The unit 7 may then be moved to rotate the sample collecting element as shown in FIG. 3B and release the sample collecting element from extension 16 of the shaft 4. After release of the sample collecting element from its connection with the shaft 4, the remainder of the sample collecting element is then inserted into the unit 7, for example by gravity by holding the sample collection unit an upright vertical position, or by pushing the sample collected element further into the unit with the end of the shaft 4. The unit is then sealed with the appropriate cover, preferably to form an airtight seal.

The sealed unit 7, having the sample collecting element 6 therein, may then be placed in the mailing package 14 which is designed to protect the sealed unit during return transport of the sealed unit to a medical facility, for example a doctor's office, hospital or laboratory, for appropriate testing of the collected sample therein.

In one embodiment, the sample collecting system further comprises an instruction sheet 20, particularly useful when the sampling system is adapted for self sampling by an individual.

In one embodiment, the sampling system of the invention is configured to allow an individual to self-collect a sample. In an additional embodiment, the self-sampling device is configured to allow an individual to collect a sample from mucous tissue. In another embodiment, the mucous tissue resides in the gynecological tract and in another embodiment the mucous tissue resides in the mouth, (e.g. cheek). The sampling system may be used by distribution to a patient, who conducts sampling and returns the sample for final laboratory analysis according to the present invention.

Example

This example examines if the same result will be obtained when gynecological smears are taken by hospital staff using previous standard procedures or using the sampling system according to the present invention, as well as if patients themselves use the sampling system.

Figure 4:
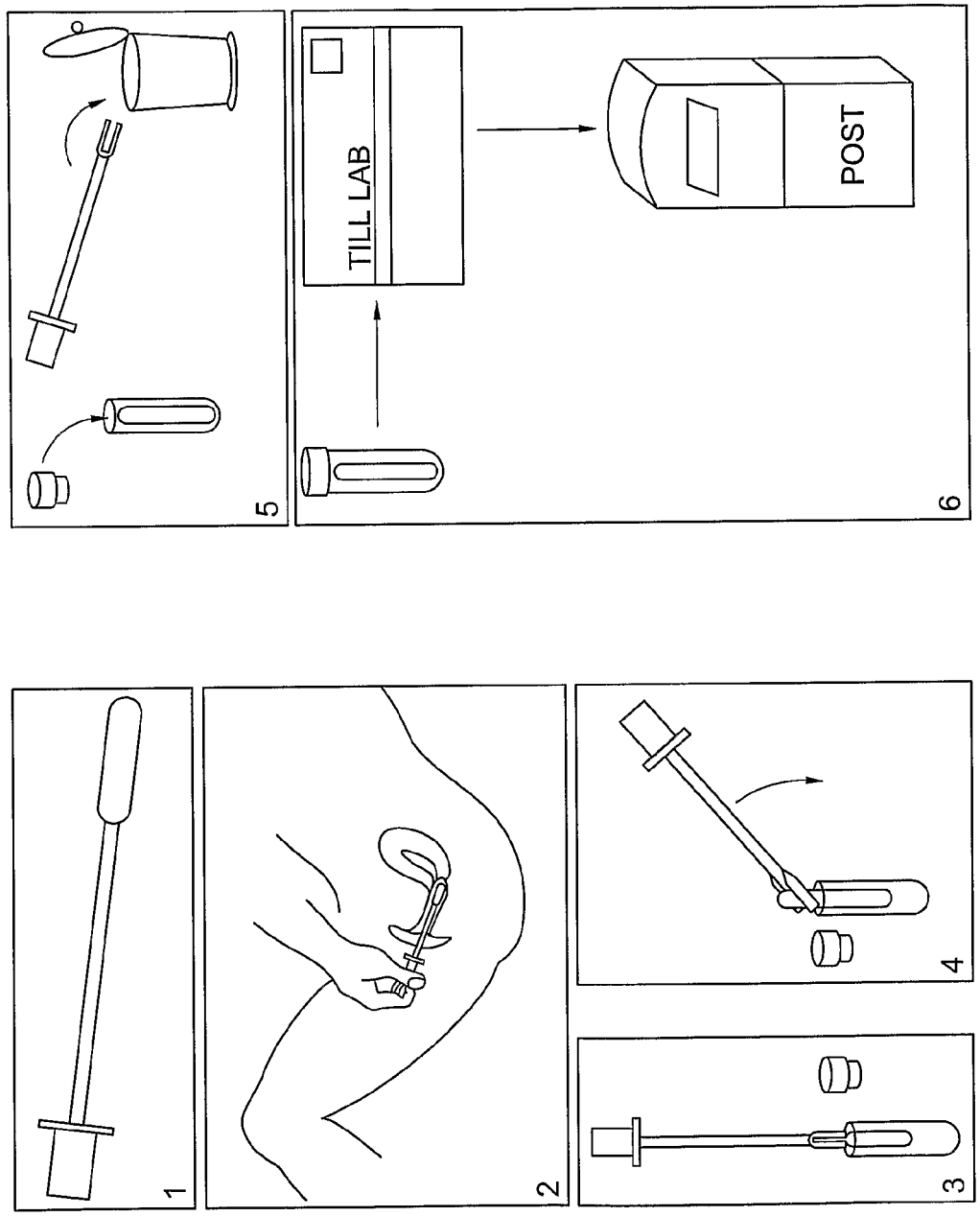
FIG. 4 is an illustration of an instruction sheet suitable for use in accordance with one embodiment of the sampling system of the invention.

Thirty six women are requested to come to the hospital for regular gynecological control and participate in the study. The hospital staff secures gynecological smears from the portio area with the use of a cytobrush. One sample is used for conventional cytological screening and the other for HPV analysis. The women take one sample themselves with the present invention following the written information as shown in FIG. 4. This sample is used for HPV analysis.

All samples are sent to the Department of Pathology, University of Uppsala. The smears collected with cytobrush by the gynecological staff and the smears collected by the women themselves with the device are analyzed for presence of HPV with the Hybrid Capture II method (Digene Diagnostics Inc., Silver Spring, Md., USA). The cytological smears are, after screening, examined for HPV using a PCR based technique.

All samples taken with previous standard procedures are scraped into test tubes and PCR buffer and proteinase K is added. When samples are taken with the device according to the present invention, the PCR buffer and proteinase K are simply added into the sealable unit, either by the user, or prior to delivery of the sampling system to a user, or upon return of the unit to, for example, a testing facility. The cells are digested at 60° C. and the DNA fraction recovered with standard methods.

The PCR amplification is performed in 100 μl volume containing standard amplification reagents. Type-specific PCR amplification is performed under conditions described by Brule et al. using GP5+/GP6+ general primers. Samples with HPV DNA amplicones are sequenced with an ABI PRISM 310 Genetic Analyzer (Applied Biosystems, Foster City, Calif.) after which the HPV type can be determined.

The results from these studies demonstrate that the women themselves can readily secure gynecological samples with the device according to the present invention. Furthermore, both cytological and PCR analysis of the samples give essentially the same result as when medical staff take the samples either using the present device or other previously well established sampling methods. It is demonstrated that the analysis can be carried out with satisfactory results three days after sampling with the device.

Thus, the sampling system is particularly advantageous for self-sampling for gynecological samples, and particularly HPV analysis. After self sampling at home, the device may be rapidly returned by mail to a hospital laboratory for HPV analysis. The sampling system according to the present invention is surprisingly well accepted, and is particularly useful for self sampling at home.

The sampling system will increase participation in the gynecological screening programs evaluating the risk of developing cervical cancer in situ. Self and home sampling will be positive from a health-economic point of view, but more importantly, increased participation will decrease the incidence of cervical cancer and also decrease the number of women who die of this disease.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

The invention claimed is:

1. A sampling system comprising:
a) a mailing package; and
b) a cell sampling device comprising:
 a. a flexible linear shaft configured to allow an individual to self-collect a sample from mucous tissue, said shaft having a first end and a second end and a handle at the first end and a longitudinal axis extending from the first end to the second end, and the second end having a shaft extension with two perpendicular prongs, each prong having an inner surface defining a groove and a protrusion, said grooves being on a same longitudinal level as each other at a proximal end of the forks and said protrusions being on a same longitudinal level as each other at a distal end of the forks;
 b. a detachable cylindrical sample collecting element having a rounded distal end and a collection element extension at a proximate end, the collection element extension dimensioned to fit in between the two prongs of the shaft extension and having two protrusions, one on each opposite side, fitting in the grooves of the shaft extension, wherein the sample collecting element was connected to the shaft extension at a connection by snapping the collecting element extension in between the forks of the shaft extension and aligning the protrusions of the collecting element extension with the grooves on the forks, and wherein the collecting element can be disconnected from the shaft extension by pivoting the shaft in relation to the collection element at the connection of shaft extension and collection element extension to release the protrusions of the collection element extension from the grooves on the forks, and wherein the collecting element has a surface formed of raised portions and grooves; and
 c. a sealable unit, wherein the unit is configured to store the sample collecting element, disconnected from the shaft and having a cell sample thereon, in a sealed form and to be received within the mailing package in a selected form.

2. The system of claim 1, wherein the shaft is configured to allow an individual to self-collect a sample from a cervix location.

3. The system of claim 1, further comprising a transport package configured to receive components a)-c) for delivery to an individual for use of the system.

4. The system of claim 3, wherein the transport package and the unit each have an identification element.

5. The system of claim 1, wherein the sample collecting element has a diameter of from 2 to 20 mm.

6. The system of claim 1, wherein the raised portions are longitudinally arranged, and at least one raised portion forms an edge at a groove capable of scraping tissue to collect a sample.

7. The system of claim 1, wherein the sealable unit comprises a unit cover for the sealing the unit.

8. The system of claim 1, wherein the sample collecting element, the shaft and the sealable unit are configured to allow the sample collecting element to be at least partially inserted within the sealable unit to keep the collecting element steady while the shaft is pivoted to disconnect the collecting element into the sealable unit without contact of the sample collecting element by an individual.

9. The system of claim 7 wherein the unit and the unit cover form an air-tight seal.

10. The system of claim 6, wherein the raised portion forms a plurality of cell and mucous collecting segments.

11. The system of claim 1 wherein the grooves of the collecting element are from 0.01 to 2 mm in width for maintaining a cell and mucous sample.

12. The system of claim 6, wherein the raised portion and the grooves of the collecting element are configured to collect a sample by insertion the collecting element in a body orifice and to hold a collected sample during withdrawal of the collecting element from the body orifice.

13. The system of claim 1 wherein the surface of the sample collecting element is abrasive and has a surface roughness of from 1 to 100 µm.

14. A sampling system comprising:
a) a preaddressed mailing package;
b) an instruction sheet;
c) a flexible, linear shaft having a first end and a second end and a longitudinal axis extending from the first end to the second end, a handle at the first end and a shaft extension with two perpendicular forks at the second end and each fork having an inner surface defining a groove;
d) a detachable cylindrical sample collecting element having (1) a rounded distal end and a surface defining a plurality of raised portions and grooves, and (2) a collecting element extension with opposite sides defining protrusions, the extensions being dimensioned to fit in between the two forks of the shaft extension, wherein the sample collecting element was connected with the shaft extension at a connection by snapping the collecting element extension in between the forks of the shaft extension and aligning the protrusions of the collecting element with the grooves on the forks, and is disconnectable from the shaft extension by pivoting the shaft in relation to the sample collecting element at the connection of the shaft extension and the collecting element extension to release the protrusions of the collecting element extension from the grooves on forks of the shaft extension;
e) a bar code unit including an air tight unit cover and being configured to receive the sample collecting element therein and to be received in the mailing package; and f) a transport package configured to receive components a)-e) for delivery to a user.

15. The sampling system of claim 14, wherein the sample collecting element and the shaft form a cell sampling device.

16. The sampling system of claim 15, wherein the cell sampling device is configured to allow an individual to self-collect a sample.

17. The sampling system of claim 16, wherein the cell sampling device is configured to allow an individual to collect a sample from mucous tissue.

* * * * *